United States Patent [19]
Rowe

[11] Patent Number: 5,246,436
[45] Date of Patent: Sep. 21, 1993

[54] MIDINFRARED LASER TISSUE ABLATER

[75] Inventor: T. Scott Rowe, Mission Viejo, Calif.

[73] Assignee: Alcon Surgical, Inc., Fort Worth, Tex.

[21] Appl. No.: 810,742

[22] Filed: Dec. 18, 1991

[51] Int. Cl.$^5$ .............................................. A61N 5/06
[52] U.S. Cl. ........................................ 606/13; 606/4; 606/14; 606/16; 606/17; 604/20
[58] Field of Search .................... 128/6, 395, 397, 398; 604/19, 20, 43; 606/2, 4, 5, 6, 13, 14, 15, 16, 17, 107

[56] References Cited

U.S. PATENT DOCUMENTS

| | | | |
|---|---|---|---|
| 3,982,541 | 9/1976 | L'Esperance, Jr. | |
| 4,207,874 | 6/1980 | Choy | |
| 4,418,688 | 12/1983 | Loeb | |
| 4,469,098 | 9/1984 | Davi | 606/17 |
| 4,559,942 | 12/1985 | Eisenberg | |
| 4,619,643 | 10/1986 | Bai | 604/43 |
| 4,694,828 | 9/1987 | Eichenbaum | |
| 4,744,360 | 5/1988 | Bath | |
| 4,846,172 | 7/1989 | Berlin | |
| 5,123,902 | 6/1992 | Müller | 606/5 |

FOREIGN PATENT DOCUMENTS

WO91/06271  5/1991  World Int. Prop. O.

OTHER PUBLICATIONS

*Holmium-YAG Laser Surgery on Experimental Vitreous Membranes*, Arch. Opthalmol., vol. 109:1605-09 (Nov. 1991) by Borirakchanyavat, Puliafito, Kliman, Margolis and Galler.

*Erbium-YAG Laser Surgery on Experimental Vitreous Membranes*, Arch. Ophthalmol., vol. 107:424,28 (Mar. 1989) by Margolis, Farnath, Destro and Puliafito.

*High-speed Photography of Er:YAG Laser Ablation in Fliud*, Invest. Ophthal. & Visual Science, 31(12):2546-50 by Stern and Puliafito.

Primary Examiner—Stephen C. Pellegrino
Assistant Examiner—Mike Peffley
Attorney, Agent, or Firm—Jeffrey S. Schira

[57] ABSTRACT

A midinfrared laser tissue ablater having an Er:YAG radiation source optically connected to a first end of a fiber optic cable, a probe with a handle and a bifurcated cannula having a first half and a second half and a generally closed, hollow tip having an opening opposite the handle, a fiber optic integrally and coaxially mounted in the probe, optically and mechanically connected to a second end of the fiber optic cable and terminating at a free end in an interior of the hollow tip, the free end having a coating with a hole so that a pulse of radiation emitted by the radiation source is directed through the fiber optic cable and the fiber optic to the free end where the pulse of radiation is reflected by the coating out the hole in the coating and into the opening in the tip, an irrigation source connected to the first half of the cannula and an aspiration source connected to the second half of the cannula.

9 Claims, 15 Drawing Sheets

TIME = 5 μSECONDS

TIME = 12 μSECONDS

TIME = 16-25 μSECONDS

TIME = ≥25 μSECONDS

TIME = 100 MILLISECONDS

MIDINFRARED LASER TISSUE ABLATER

BACKGROUND OF THE INVENTION

The present invention relates generally to microsurgical instruments and more specifically to laser microsurgical instruments for use in cutting thin tissues or membranes. Prior to the present invention, thin tissue such as vitreous membranes were generally cut with a mechanical cutter or surgical knife. In the case of posterior segment surgery of the eye, a mechanically or pneumatically driven microscissors generally is used. However, vitreous surgery of tissues tightly adhered or adjacent to the retinal surface is very exacting because of the possibility of retina injury. As a result, a need exists for an alternative to these mechanical systems.

Midinfrared lasers long have been used for ablation of biological tissue because they generally emit radiation with a wavelength near the several water absorption peaks, resulting in an extremely short tissue penetration depth, generally between 1 micron ($\mu$m) and 500 $\mu$m. Examples of such lasers include the hydrogen fluoride laser, the erbium:yttrium aluminum garnet (Er:YAG) laser, the holmium:yttrium aluminum garnet (Ho:YAG) laser, the Raman-shifted neodymium:yttrium aluminum garnet (Nd:YAG) laser and the $CO_2$ laser lasing at a wavelength of 10.6 $\mu$m. However, the $CO_2$ laser is not as useful as some other midinfrared lasers as a tissue ablater because the absorption depth of water at the relevant $CO_2$ laser wavelength of approximately 10.6 $\mu$m is ten times greater than at the wavelength emitted by the Er:YAG laser.

The Nd:YAG laser has been shown to be useful for photodisruption in the anterior segment of the eye, but generally is considered unacceptable for use in the posterior segment of the eye because of possible cavitation, acoustic and shock-wave effects and insufficient light divergence at the retina. Er:YAG lasers have been shown in experimental vitrectomies to be effective at cutting vitreous membranes. However, in some cases, retina injury resulted even though the fiber optic tip was held more than 1 mm from the surface of the retina. This extremely large damage zone is the result of gaseous bubble formation at the fiber optic tip.

As discussed by Lin, et al. in their article *High-speed Photography of Er:YAG Laser Ablation in Fluid: Implication for Laser Vitreous Surgery*, Invest. Oph. & Visual Sciences, 31(12):2546-2550 (Dec. 1990), when the Er:YAG laser is pulsed, the laser output consists of one or several submicrosecond spikes separated by a few microseconds. The first spike heats the liquid at the fiber optic tip, forming a bubble of hot gas. Subsequent spikes propagate readily through the bubble until they strike the outer liquid boundary of the bubble, thereby expanding the size of the bubble and allowing the thermal and mechanical energy to be transmitted to and damage an area of tissue much larger than that to be treated or cut. This article suggests either using low energy (below 0.5 mJ) but inefficient laser pulses and/or a shielded fiber optic tip to control or limit the expansion of the bubble. While a shielded tip might be effective in reducing the *surface* area of the tissue exposed to the bubble, the shielded tip does not affect the dwell time of the bubble at the tissue surface, likely resulting in a smaller yet *deeper* area of tissue damage. Therefore, neither the use of low energy pulses nor the shielded tip disclosed by Lin, et al. provide a laser tissue ablater that cuts tissue efficiently while minimizing collateral tissue damage.

In their article *Erbium-YAG Laser Surgery on Experimental Vitreous Membranes*, Arch. Oph., Vol. 31, pages 424-28, (Mar. 1989), Margolis, et al., discuss the use of a shielded tip in combination with an Er:YAG laser. A pulse energy of 3.6 mJ and a pulse repetition rate of 2 Hz was found to give the best tissue cutting results. Higher pulse repetition rates resulted in hot jets of vitreous flow to the retina that the authors believed caused the observed retinal lesions. The authors did not attempt to cut tissue closer than 1000 $\mu$m to the retinal surface despite their recognition that many ophthalmic surgical procedures require cutting membranes less than 500 $\mu$m from the retina.

Similarly, in their article *Holmium-YAG Laser Surgery on Experimental Vitreous Membranes*, Arch. Oph., Vol. 109, pages 1605-09 (Nov. 1991), Borirakchanyavat, et al., discuss the use of a Ho:YAG laser to cut vitreous membranes. However, the authors found that the most efficient tissue cutting occurred at a pulse repetition rate of between 1 Hz and 2 Hz and a pulse energy of greater than 60 mJ. At this relatively high pulse energy, tissue cutting without retina damage was limited to distances of greater than 0.5 mm from the retina despite the use of a shielded tip. Furthermore, the Ho:YAG laser emits radiation at a wavelength of approximately 2.12 $\mu$m. The tissue absorption length at this wavelength is approximately 430 $\mu$m, far greater than the tissue absorption length of approximately 1 $\mu$m of the radiation emitted by the Er:YAG laser. This relatively long tissue absorption length makes it difficult to irradiate thin membranes without the radiation penetrating deeper into and damaging surrounding tissue.

Accordingly, a need continues to exist for an efficient midinfrared laser tissue ablater that reduces the amount of collateral tissue damage while permitting the cutting of tissues tightly adhered or adjacent to the retinal surface.

BRIEF SUMMARY OF THE INVENTION

The present invention improves upon the prior art by providing a midinfrared laser tissue ablater having a probe with a bifurcated irrigation/aspiration cannula surrounding a coaxial fiber optic having an energy transmissive core and a reflective cladding connected on the end opposite the cannula to one end of a fiber optic cable. The upper half of the cannula forms an irrigation fluid flow channel and the lower half of the cannula forms an aspiration fluid flow channel. The cannula terminates in a generally blunt, hollow tip with which the irrigation and aspiration channels and the tip of the fiber optic core communicate. The probe tip is closed except for a small, circular opening near the entrance to the aspiration channel that allows the interior of the probe tip to communicate with the exterior of the probe tip. The tip of the fiber optic core is sa generally conical and coated with a reflective material such as gold so that radiation exiting the tip is reflected downward through a small hole in the coating and toward the opening in the probe tip. The radiation source is optically connected to the other end of the fiber optic cable and may be any suitable laser emitting radiation with a wavelength near the 2.9 $\mu$m water absorption peak, such as a $Er^{+3}$:YAG laser having $\lambda = 2.94$ $\mu$m. The probe also contains an irrigation fluid port and an aspiration fluid port that communicate with the irrigation fluid channel and the aspiration fluid channel, respectively. The irrigation fluid port and the aspiration fluid port are connected by flexible tubings to a control console containing an irrigation fluid source, a source of vacuum for aspiration and a means to control the flow rates of the irrigation fluid and the aspiration fluid through the probe.

In use, the cannula tip is placed on top of the surgical site so that the opening in the probe tip rests against the tissue to be ablated and the irrigation and aspiration fluid flow rates are adjusted at the control console so that the hollow interior of the probe tip is continuous bathed in irrigation fluid as it flows out the irrigation channel and into the aspiration channel. As the laser is pulsed, the radiation is transmitted to the probe tip through the fiber optic cable and the fiber optic core in the probe. As the radiation exits the hole in the coated tip of the fiber optic core, the radiation is directed downward toward the opening in the probe tip by the coating and is absorbed by the irrigation fluid at the interface of the fiber optic core and the irrigation fluid, forming a gas bubble. Subsequent spikes of radiation (occurring approximately every 5-6 microseconds ($\mu$sec.) over a 25 $\mu$second period during a typical 100 millisecond laser pulse) travel through the gas bubble and are absorbed by the irrigation fluid at the liquid/gas interface on the side of the bubble opposite the hole in the fiber optic tip coating, thereby continuing to expand the bubble. As the bubble expands so that it just touches or very nearly touches the surface of the tissue to be ablated, the next spike of radiation travels through the bubble and irradiates the tissue at the tissue/bubble interface. The irrigation/aspiration flows within the hollow cannula tip are controlled by the console so that just as the bubble expands out of the opening in the probe tip and tissue irradiation occurs, the bubble is drawn into the aspiration channel and away from the surgical site before it can grow any larger and permit subsequent spikes of radiation to cause collateral tissue damage or allow the hot gas bubble to expand beyond the tip and contact surrounding tissue. Further, the dwell time of the bubble on surface 62 is minimized. The bubble formation/aspiration cycle occurs once for every laser pulse and generally is completed in a 20-25 $\mu$sec. period. This process is repeated once during every 100 millisecond laser pulse cycle.

Accordingly, one objective of the present invention is to provide a high efficiency midinfrared laser tissue ablater suitable for cutting thin membranes.

Another objective of the present invention is to provide a midinfrared laser tissue ablater having a probe with a bifurcated irrigation/aspiration cannula.

Another objective of the present invention is to provide a midinfrared laser tissue ablater having a probe with a fiber optic cable coaxially mounted within an irrigation/aspiration cannula.

Still another objective of the present invention is to provide a midinfrared laser tissue ablater having a probe that reduces collateral tissue damage.

A further objective of the present invention is to provide a midinfrared laser tissue ablater that quickly removes the gas bubbles formed by the lasers spikes from the surgical site.

These and other and further advantages and objects of the present invention will become apparent form the drawings, detailed description and claims that follow.

DETAILED DESCRIPTION OF THE INVENTION

Figure 1:
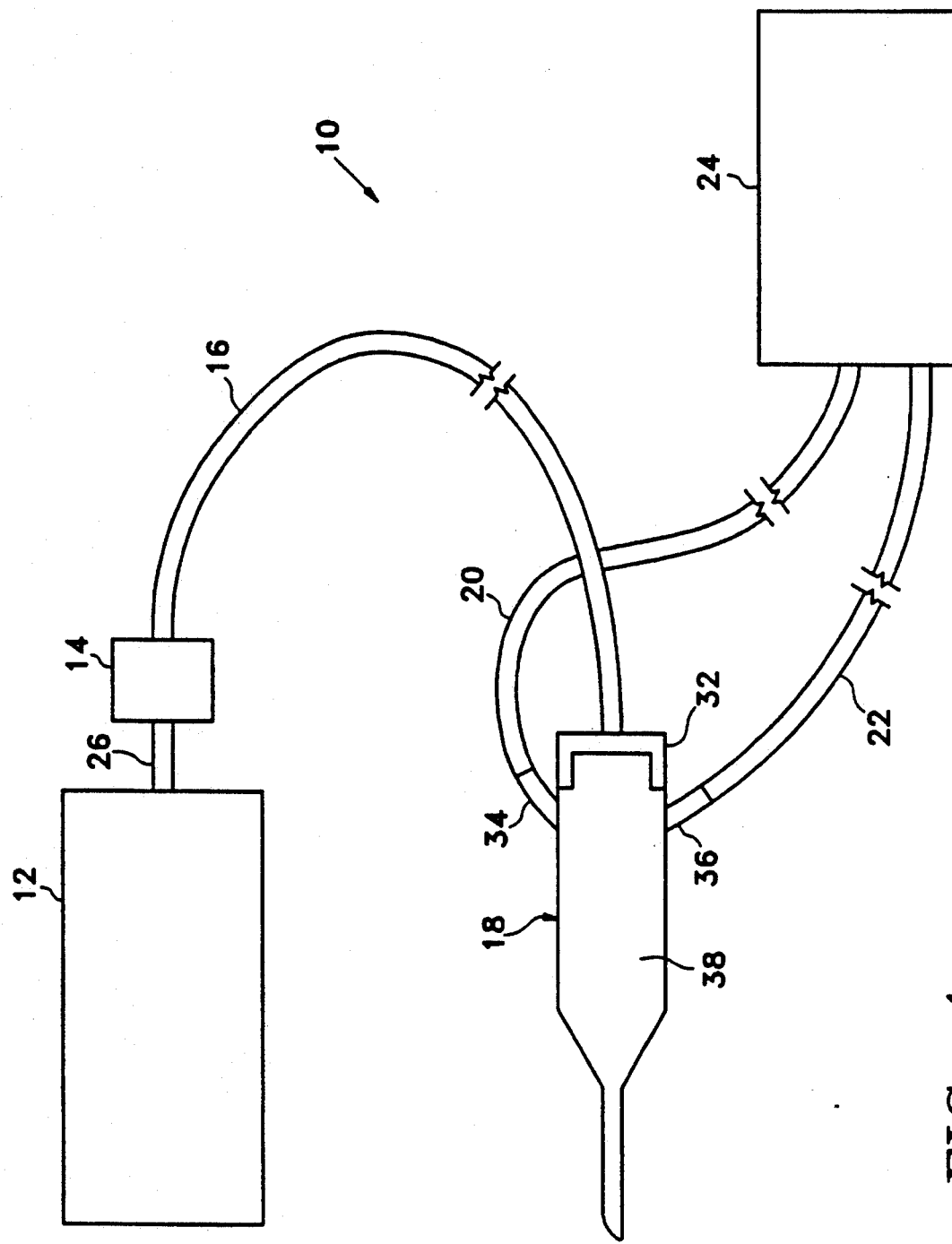
FIG. 1 is a schematic view of the laser tissue ablater of the present invention.

As can be seen in FIG. 1, laser tissue ablater 10 of the present invention generally consists of radiation source 12, optical connector 14, fiber optic cable 16, probe 18, irrigation line 20, aspiration line 22 and irrigation/aspiration source 24. Radiation source 12 may be any laser emitting radiation with a wavelength in the midinfrared band and is preferably a laser emitting radiation near the water absorption peak of $\lambda=2.9$ $\mu$m. An $Er^{+3}$:YAG laser having $\lambda=2.94$ $\mu$m is particularly well-suited but any other suitable laser may also be used. Preferably, radiation source 12 is capable of producing deposited pulse energies of approximately between 0.5 mJ and 4.0 mJ and has a pulse repetition rate of around 10 Hz. This repetition rate results in one pulse approximately every 100 milliseconds and a pulse duration of approximately 25 $\mu$sec. Output 26 from radiation source 12 is directed to fiber optic cable 16 by optical connector 14. Optical connector 14 may be comprised of a lens and a mechanical coupling, and is preferably a zinc selenide lens with the appropriate numerical aperture (NA). Fiber optic cable 16 may be any commercially available fiber optic cable and is preferably a fluorozirconiate fiber with a 200 $\mu$m core and a 0.22 NA.

Figure 2:
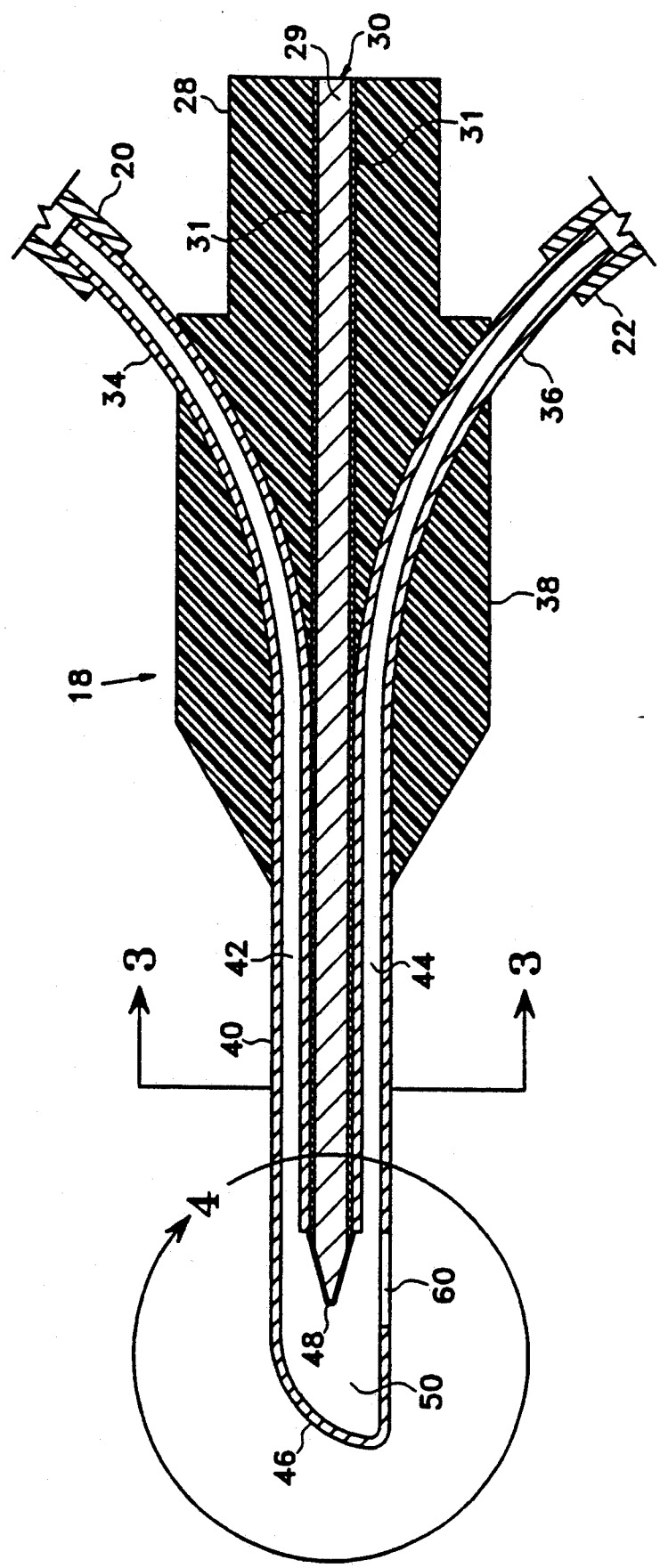
FIG. 2 is a longitudinal cross section view of the probe of the present invention illustrated in FIG. 1.

Cable 16 connects to handle 38 of probe 18 at end 28 by use of connector 32 that may a bayonet connector, a ferrule connector or any other suitable, commercially available connection device, so that cable 16 optically communicates with fiber optic 30 in probe 18. Irrigation line 20 and aspiration line 22 connect at one end to ports 34 and 36, respectively, in handle 38, as can be seen in FIG. 2 and, as shown in FIG. 1, to irrigation/aspiration source 24 at the other end. Lines 20 and 22 may be made of any suitable flexible material such as medical grade rubber, silicone rubber or soft plastic. Alternatively, lines 20 and 22 may be made of thin-walled, flexible stainless steel or titanium tubing, for use with fast rise time venturi pump aspiration systems. Irrigation/aspiration source 24 may be any suitable modified commercially available microsurgical irrigation/aspiration control device such as the Series Ten Thousand Ocutome or Series 9001 Irrigation/Aspirator, both available from Alcon Surgical, Inc., Fort Worth, Tex. 76134.

Figure 3:
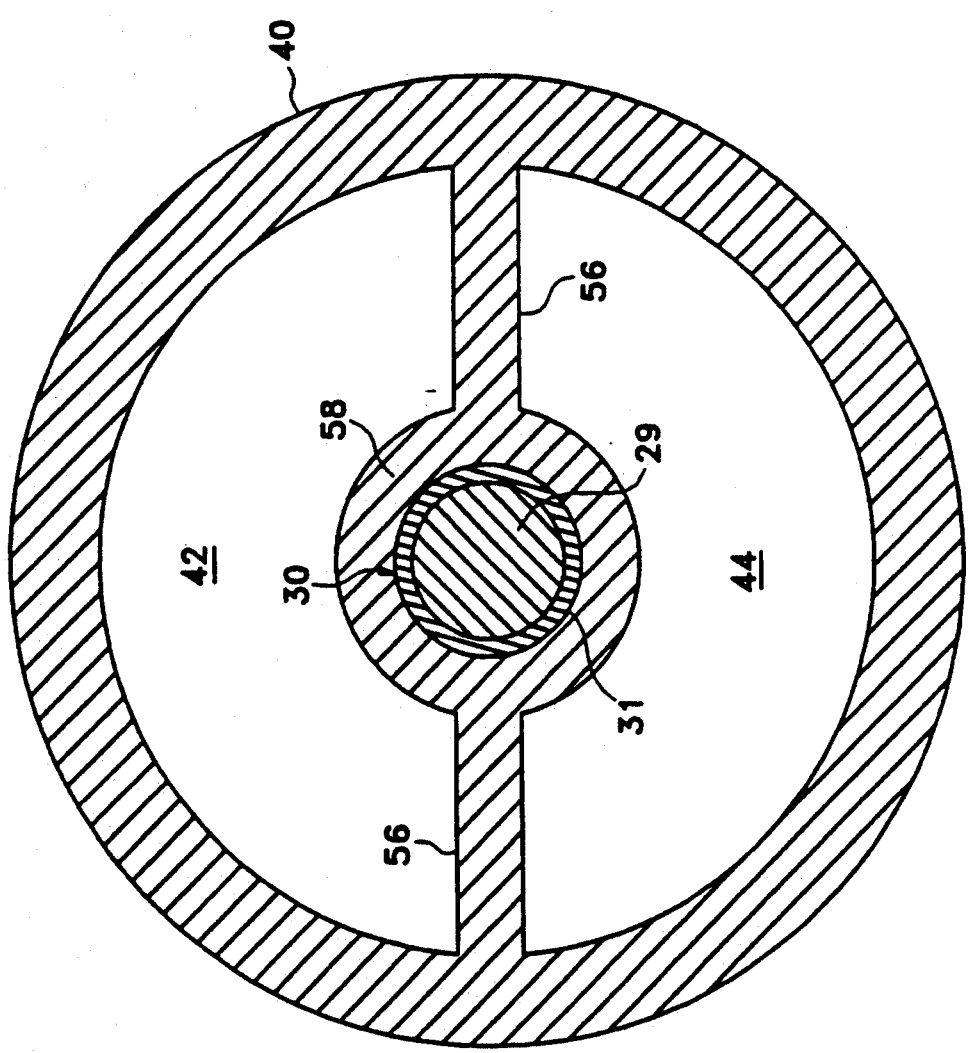
FIG. 3 is a transverse cross section of the probe cannula taken at line 3—3 in FIG. 2.

As can be seen best in FIG. 2, probe 18 generally consists of handle 38, irrigation port 34, aspiration port 36, fiber optic 30 and hollow, bifurcated cannula 40. Irrigation ports 34 and 36 extend through handle 38, which is preferably made from vacuum formed or injection molded plastic such as ABS, communicate with opposing, sealed channels 42 and 44 in cannula 40, respectively, and are preferably made of titanium or stainless steel. Cannula 40 terminates at closed, rounded tip 46 opposite handle 38 having an opening 60 and preferably has an outside diameter of between approximately 0.032 inches and 0.036 inches and preferably is made of titanium or stainless steel. Opening 60 generally is between approximately 50 μm and 200 μm in diameter with 100 μm being preferred. As can be seen in FIG. 3, channels 42 and 44 are separated and sealed from each other by longitudinal partition wall 56 having an integrally formed coaxial tube 58 into which fiber optic 30 is telescopically inserted.

As can be seen in FIGS. 4A–4F, fiber optic 30 comprises a core 29 and a cladding 31 and terminates at generally conical free end 48 in interior 50 of tip 46. Fiber optic 30 preferably has a diameter of approximately 400 μm and a 0.22 NA, core 29 is preferably a low hydroxyl fused-silica fiber and cladding 31 is preferably fluorinated low hydroxyl fused-silica, but other suitable fiber optic core and cladding materials and diameters may also be used. Free end 48 need not be conical and, alternative, may be rounded, chamfered or attached to a micro-ball lens. Free end 48 of core 29 has an optically reflective coating 52, such as gold, silver, enhanced aluminum or a dielectric, so that all the radiation emitted out end 48 is reflected through hole 54 in coating 52 on the lower side of end 48. Hole 54 may be of any suitable diameter of approximately between 25 μm and 150 μm with 50 μm being preferred.

Figure 4A:
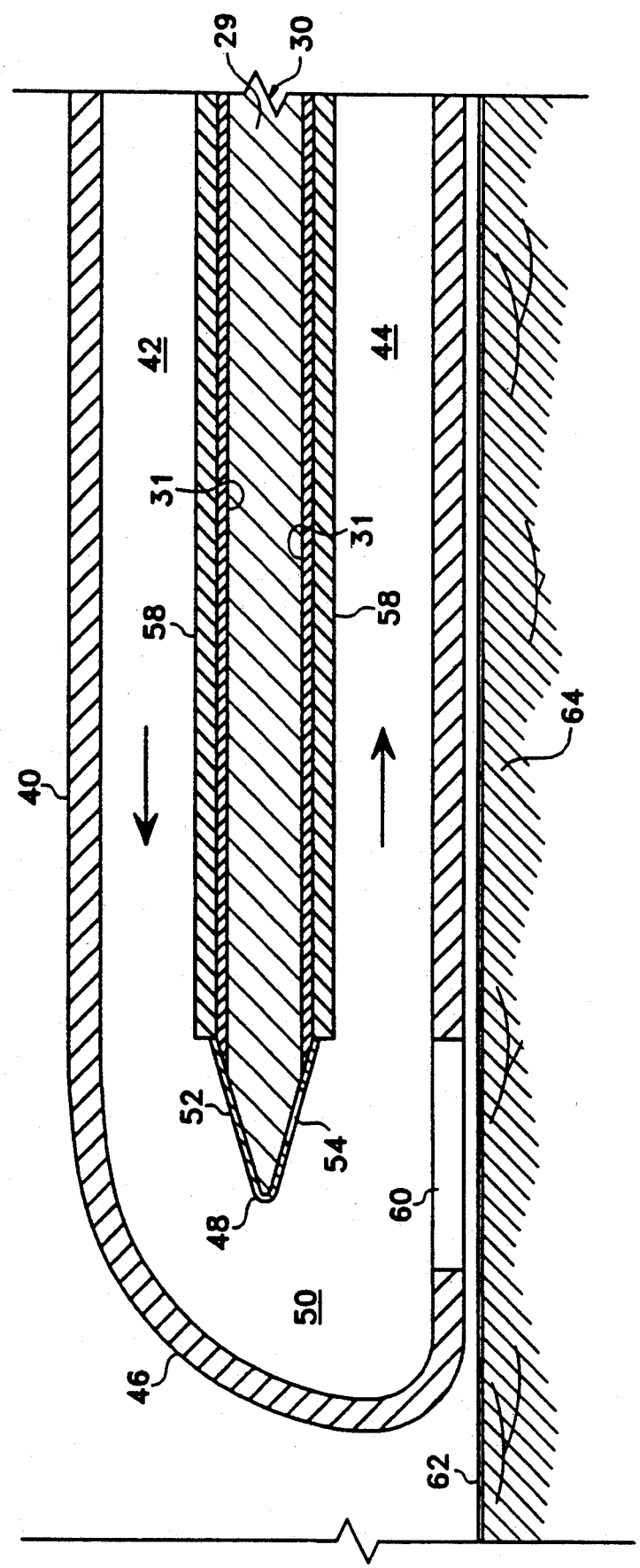
FIGS. 4A-4F are exploded cross sectional views of the cannula tip taken over time at circle 4 in FIG. 2.
Figure 4B:
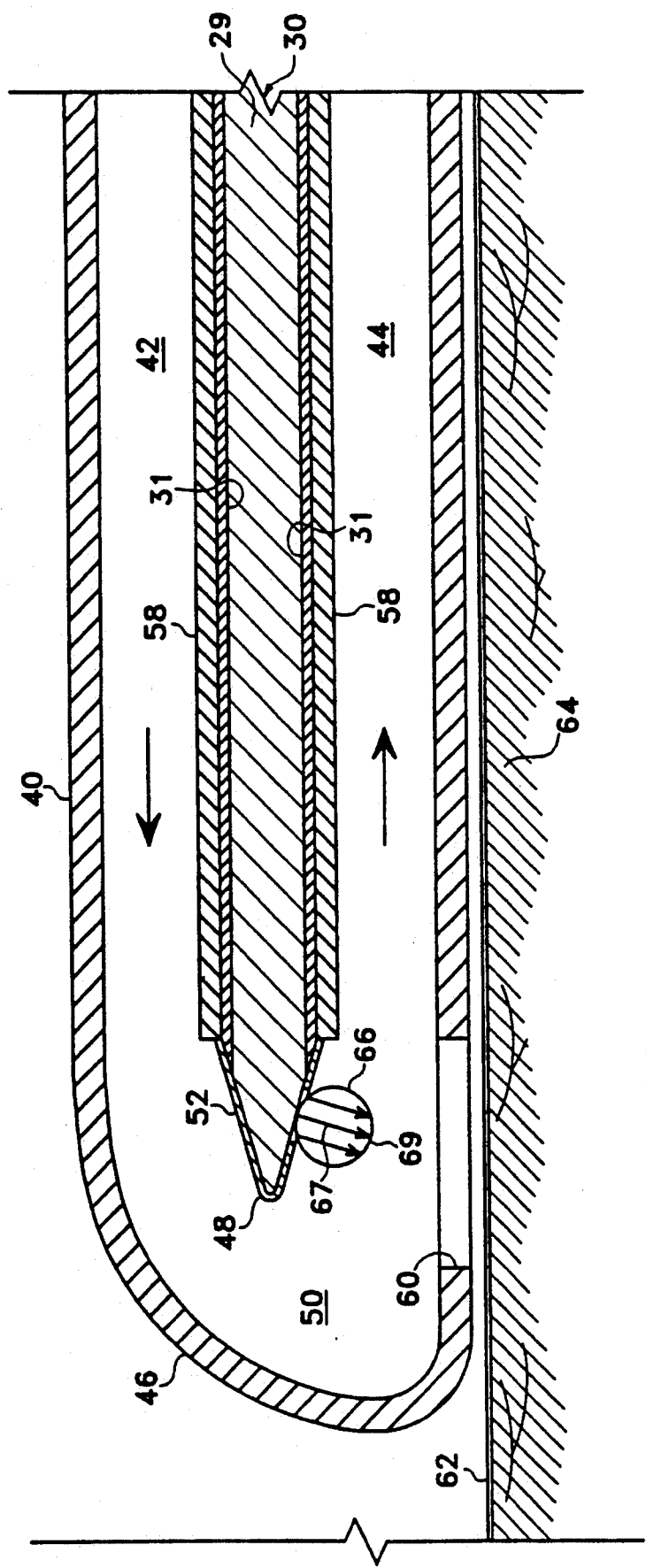
Figure 4C:
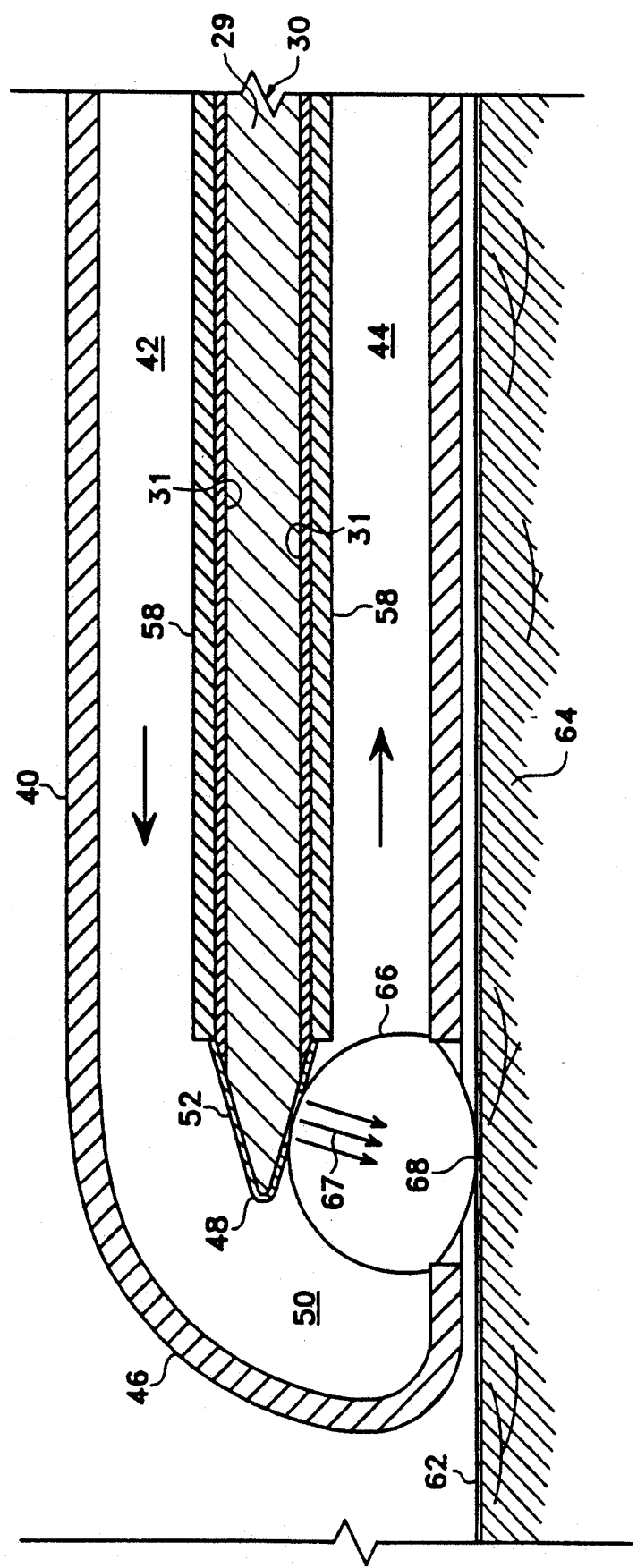
Figure 4D:
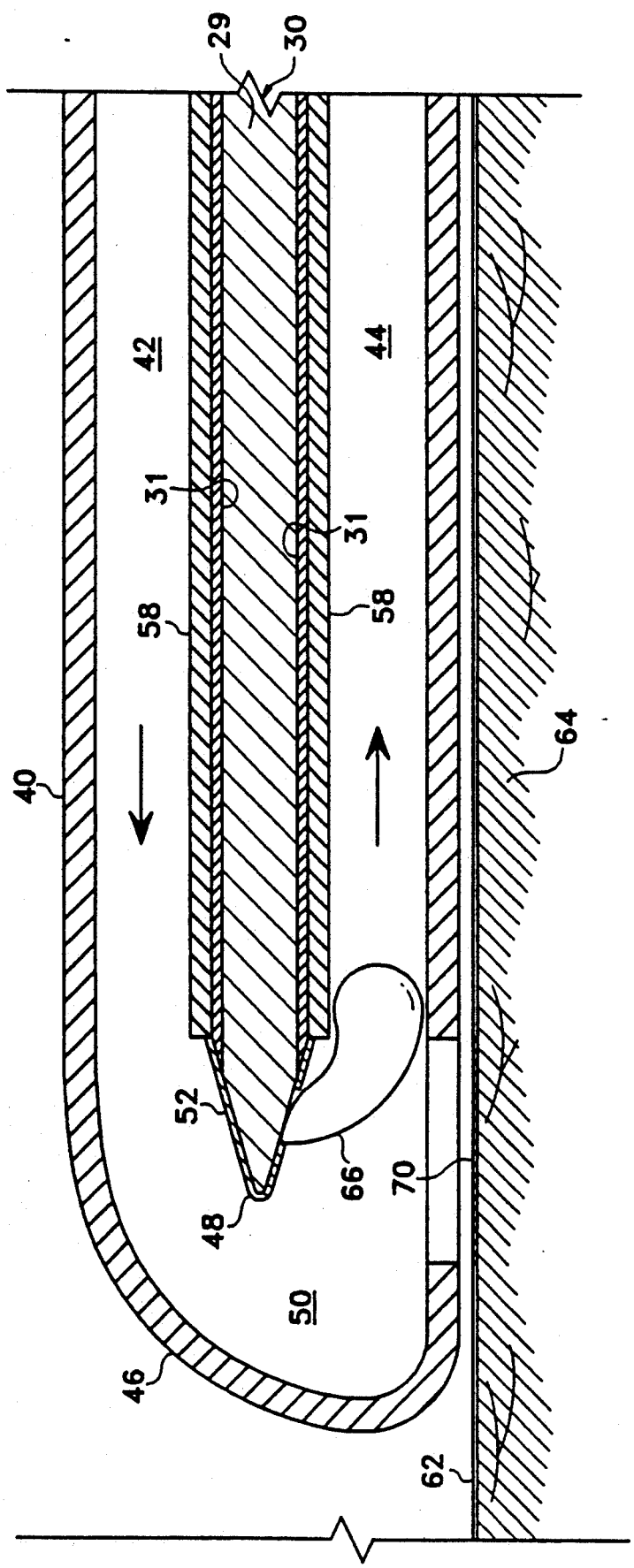
Figure 4E:
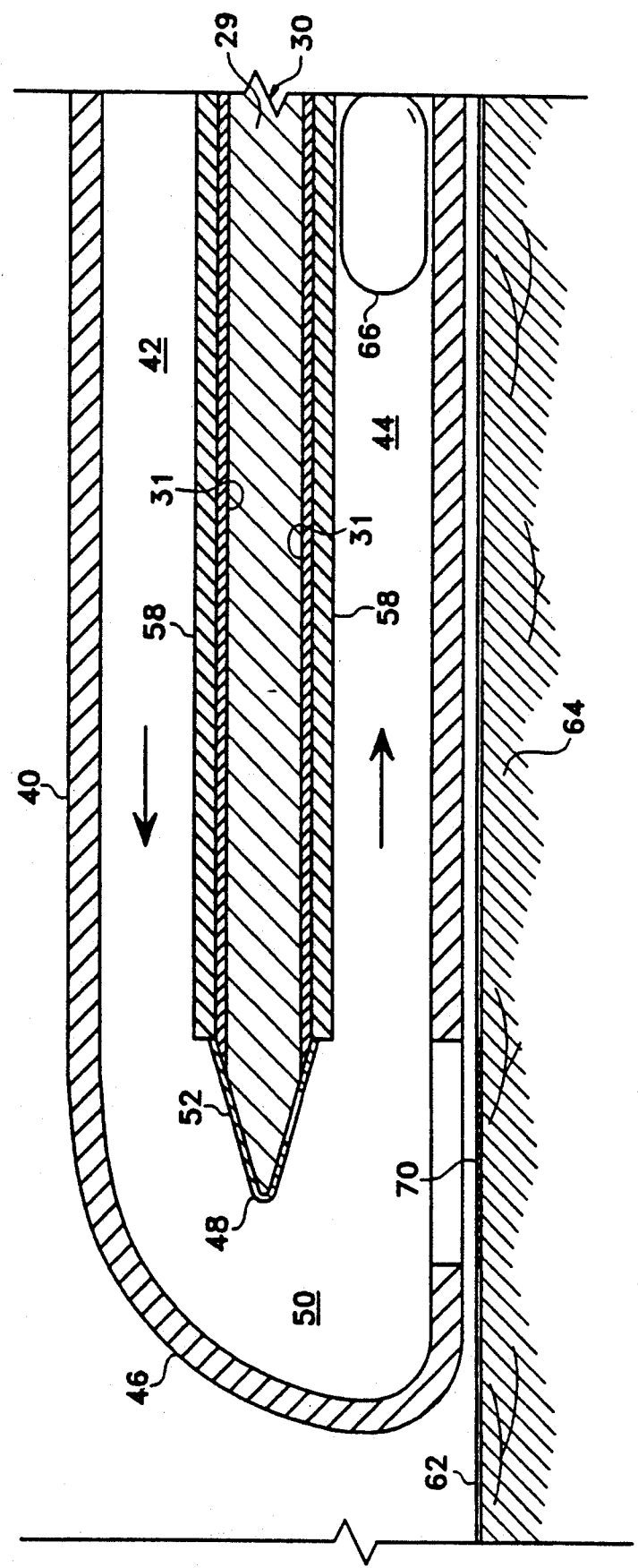
Figure 4F:
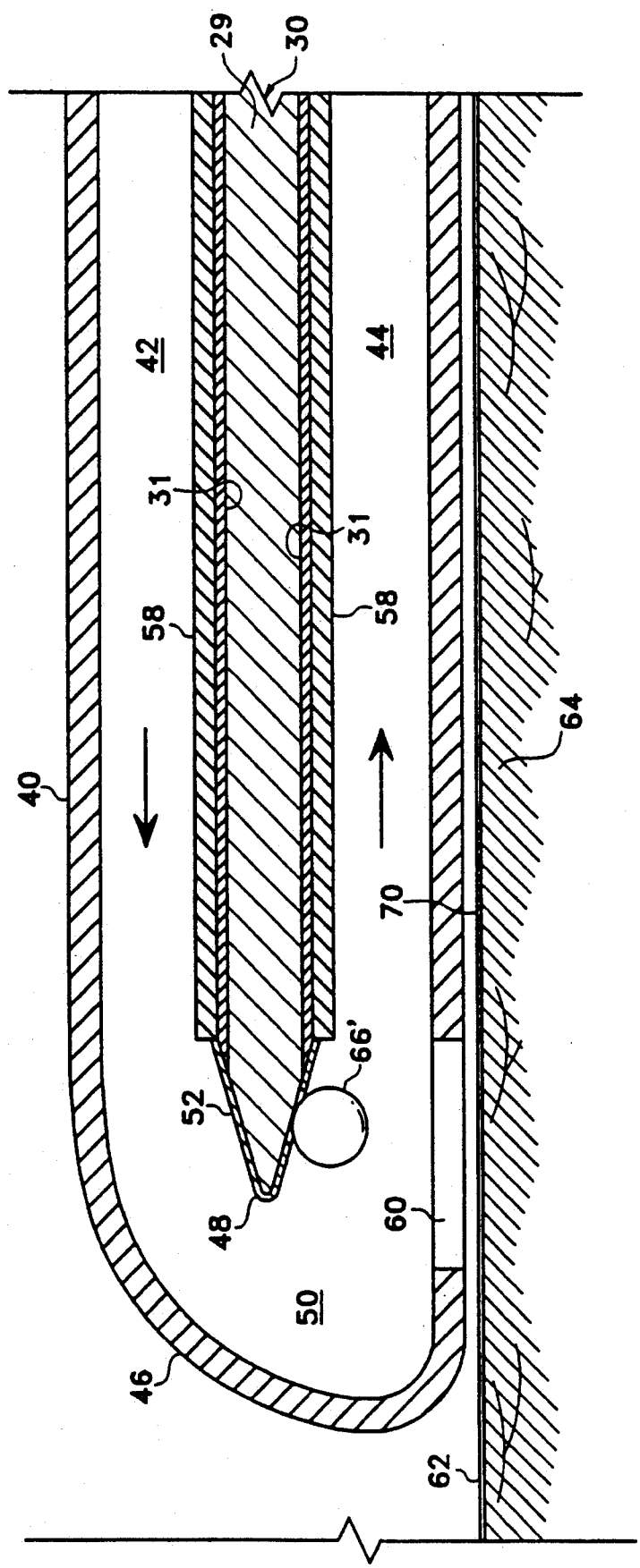
Figure 5A:
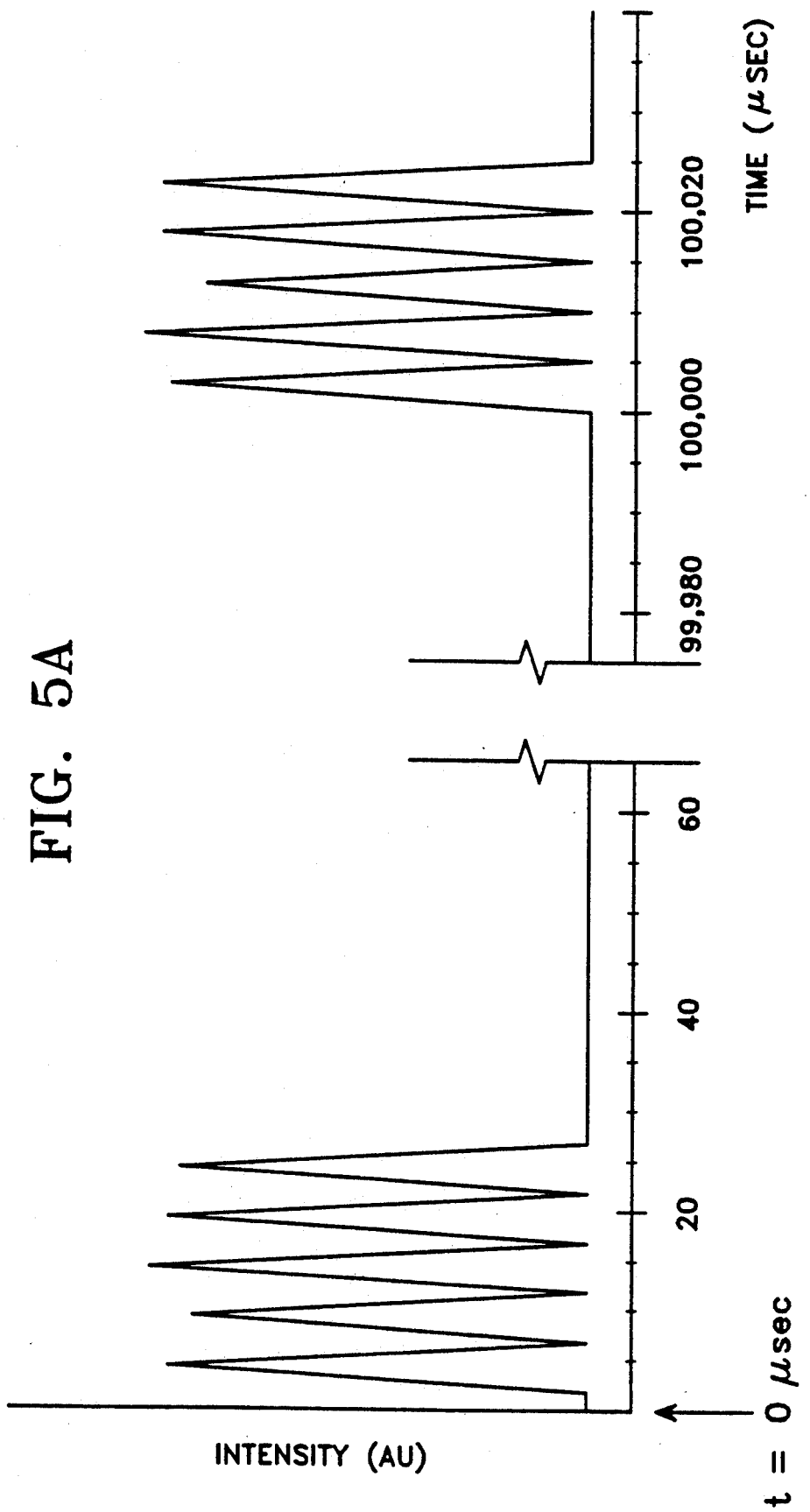
FIGS. 5A-5F are representations of an oscillograph of the laser spikes over the time period illustrated in FIGS. 4A-4F.
Figure 5B:
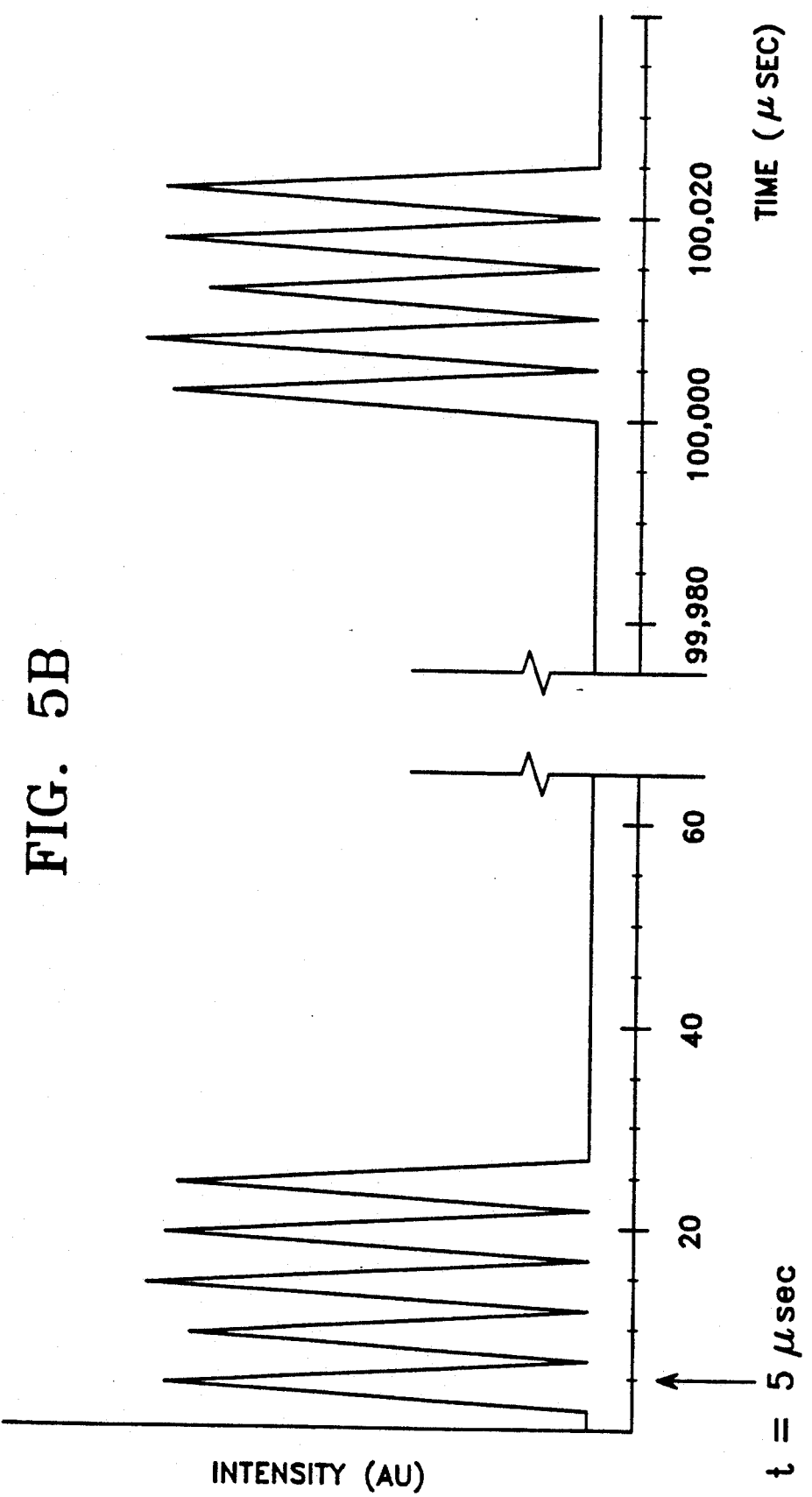
Figure 5C:
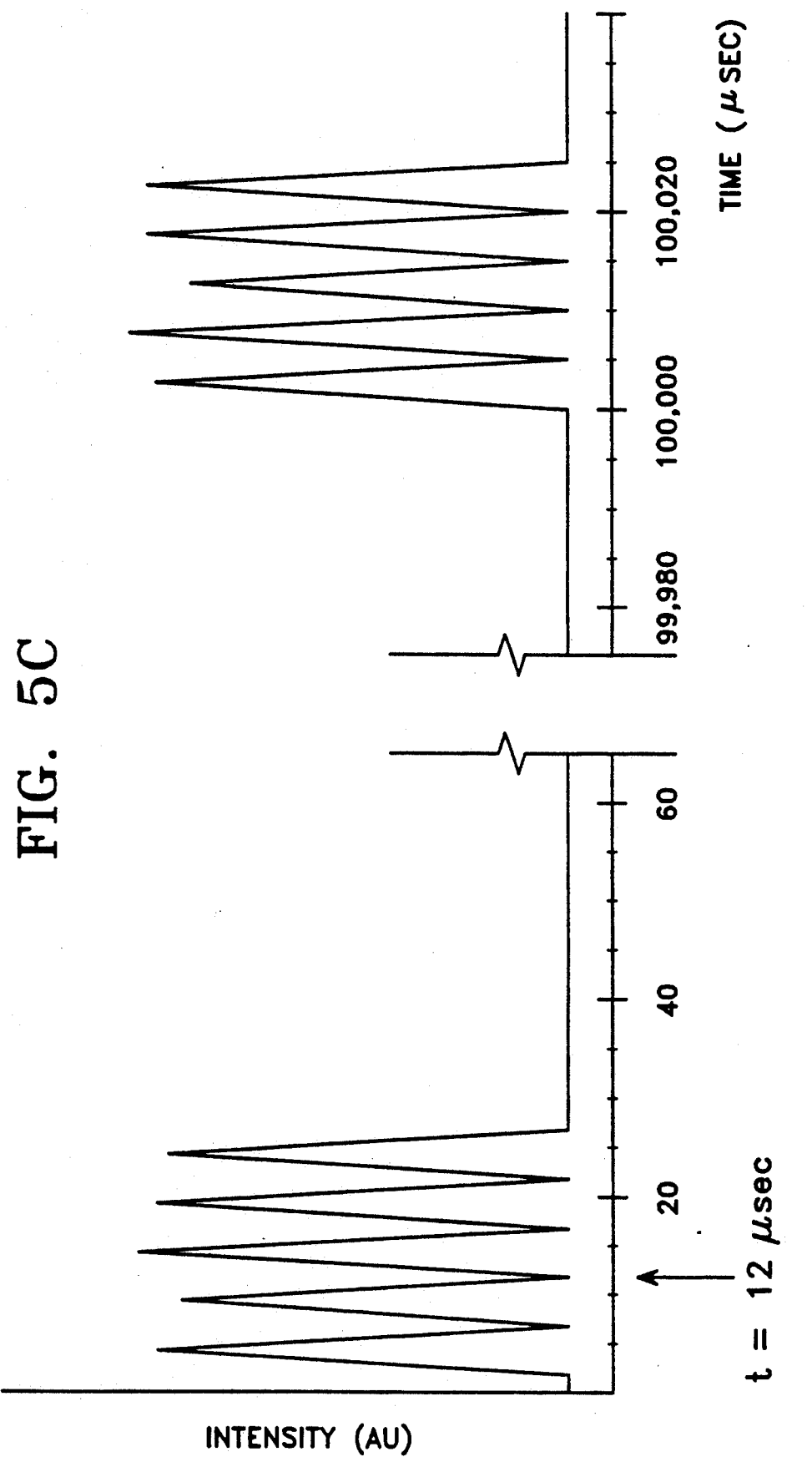
Figure 5D:
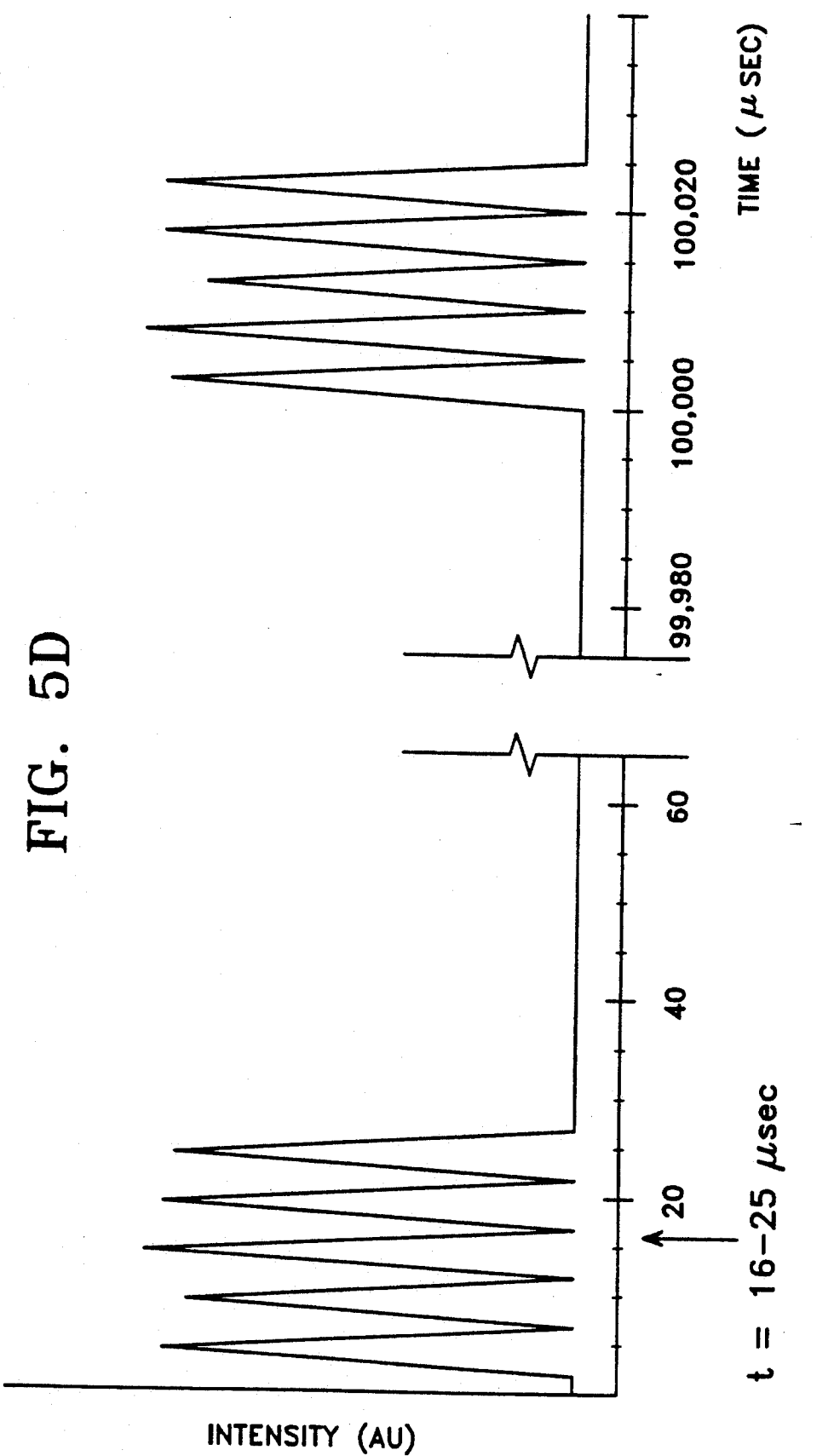
Figure 5E:
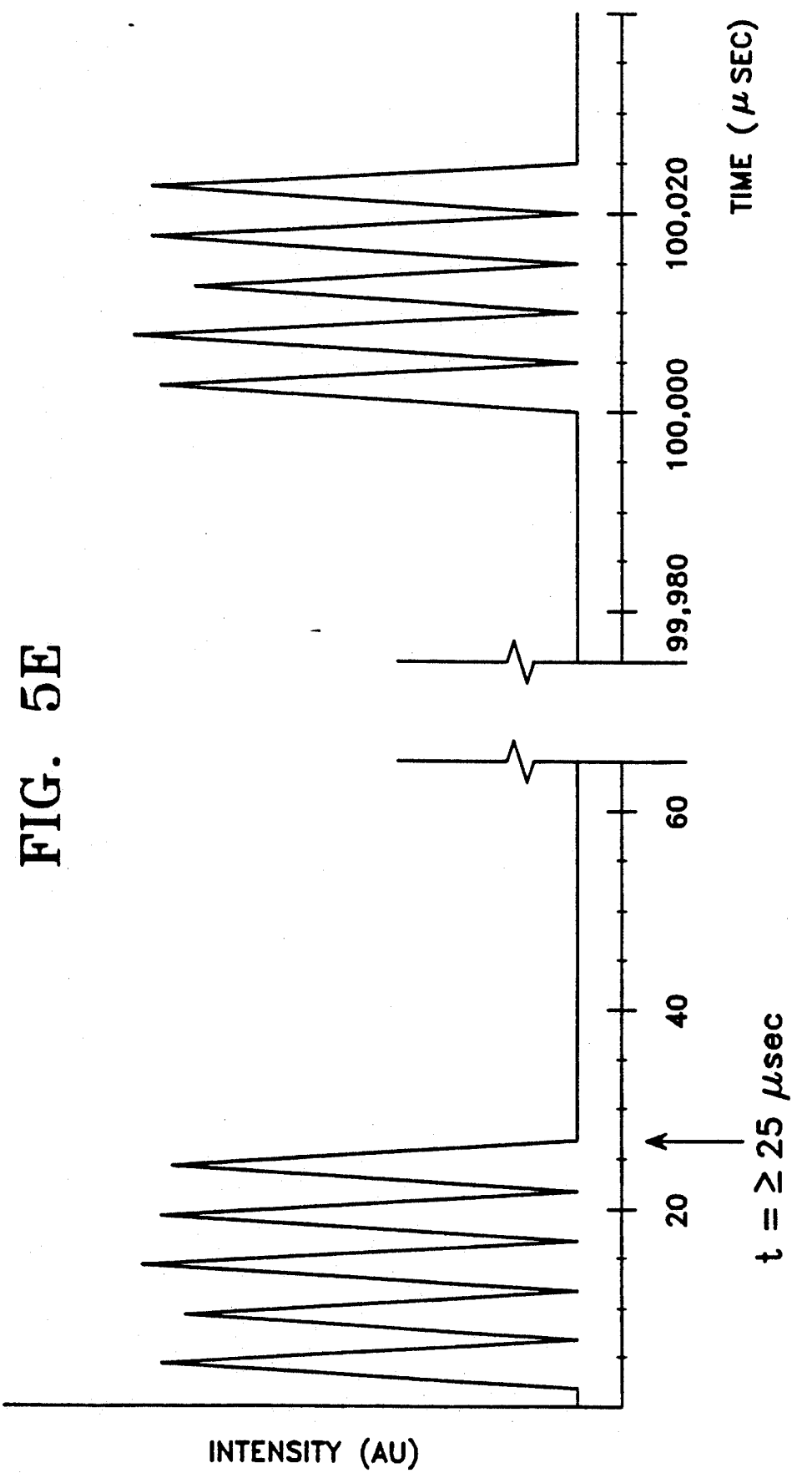
Figure 5F:
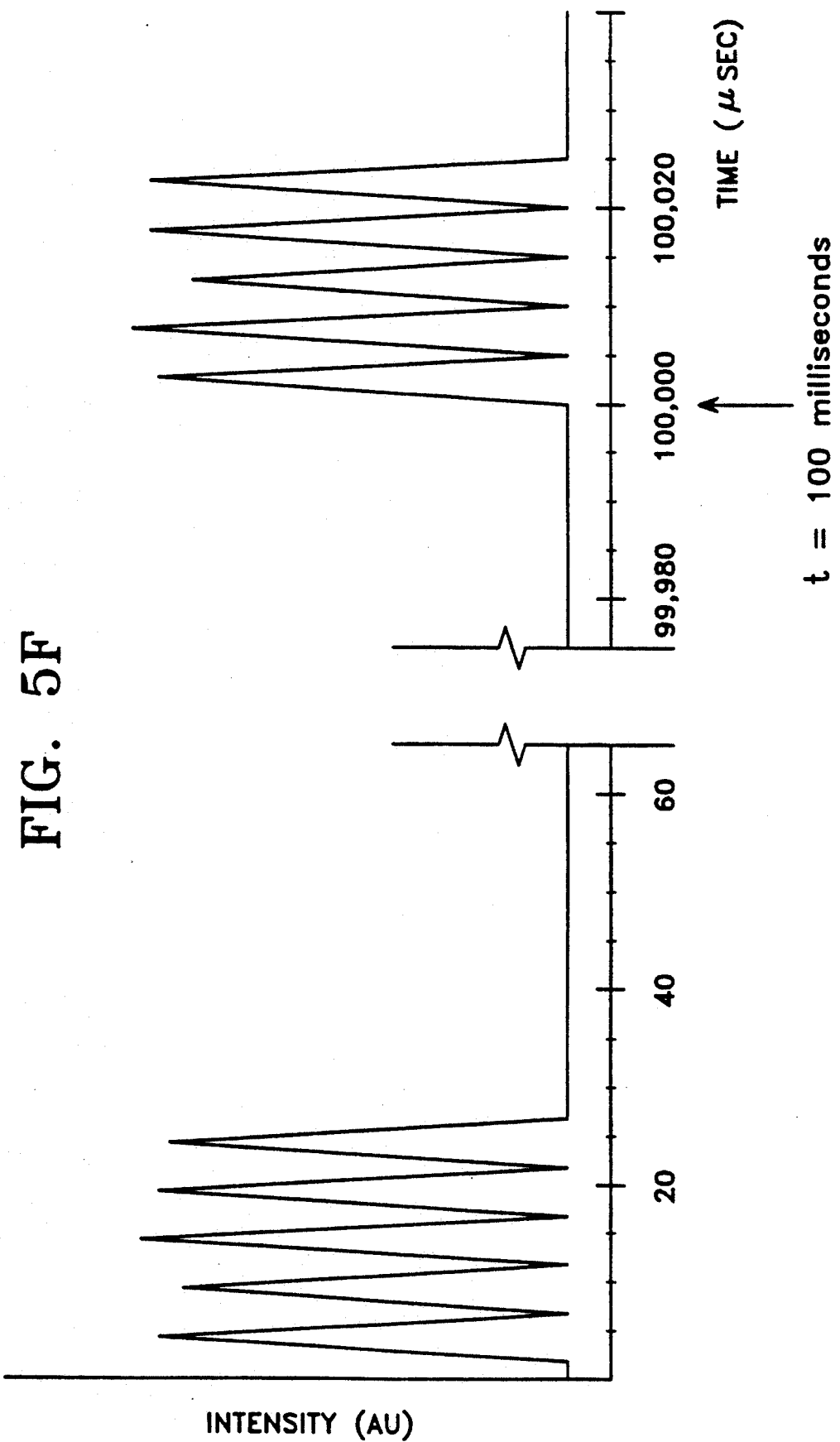

In use, tip 46 of cannula 40 is placed so that opening 60 is adjacent to or in contact with membrane surface 62 on retina tissue 64 to be ablated. As can be seen in FIGS. 4A and 5A, at time equal to 0 μsec., just prior to pulsing radiation source 12, no bubbles exist within interior 50 of tip 46 and the irrigation fluid flowing into tip 46 through channel 42 is aspirated out past the surgical site through aspiration channel 44. As can be seen in FIGS. 4B and 5B, once radiation source 12 is pulsed, the radiation pulse travels through optical connector 14, fiber optic cable 16, connector 32 and fiber optic 30 to free end 48, where the radiation is directed out hole 54 by coating 52. Within 5 μsec. after radiation source 12 is pulsed, a gaseous bubble 66 is formed at hole 54. Bubble 66 continues to expand over time as additional spike 67 of radiation from source 12 exits hole 54 and strikes liquid/gas interface layer 69 on the side of bubble 66 opposite hole 54 so that within approximately 12 μsec. after source 12 is pulsed, as can be seen in FIGS. 4C and 5C, bubble 66 has expanded to a diameter of around 800 μm and is very near (e.g. ≦1 μm) or just touching surface 62 of tissue 64 through opening 60 in tip 46. As bubble 66 nears or touches membrane surface 62, the next spike 67 from source 12 travels through bubble 66 and irradiates surface 62 at tissue/bubble interface zone 68, thereby ablating membrane surface 62 in zone 68. However, further expansion of bubble 66 outside of opening 60 will undesirably enlarge ablation zone 68 or cause thermal damage to tissue 64 under surface 62. To reduce thermal damage to surrounding tissue 64, as can be seen in FIGS. 4D and 5D, the flow of irrigation a fluid into and out of tip 46 is precisely controlled, for example, at a flow rate of approximately 325 cm$^3$ per minute, so that at around 16–25 μsec. after source 12 is pulsed, bubble 66 is drawn into channel 44, away from surface 62 and out of the surgical site, leaving only a shallow area 70 of ablated tissue. The surface tension of the surface of bubble 66 prevents bubble 66 from breaking up as it is aspirated from the surgical site. As can be seen in FIGS. 4E and 5E, by around 25 μsec. after source 12 is pulsed, bubble 66 has been drawn well down channel 44 so that by 100 milliseconds after the first spike of radiation from the first laser pulse began to form bubble 66 (as shown in FIGS. 4F and 5F), the first spike of radiation from a second laser pulse forms subsequent bubble 66'. While the ablation products are aspirated through channel 44 in cannula 40, the trans-sected tissue 70 is removed from the surgical site by a second, larger aspiration probe (not shown).

The duration of a typical laser pulse is approximately 25 μsec. The number of radiation spikes contained in a single laser pulse will vary with the pulse energy. At a deposited pulse energy of approximately 0.5 mJ, the laser pulse may contain only one or two spikes 67 near the peak of the flash lamp pulse and thus be relatively inefficient at ablating tissue. Higher deposited pulse energies (e.g., ≧1.0 mJ) result in spikes 67 occurring every 5–6 μsec. and are, therefore, more efficient at ablating tissue. Very high deposited pulse energies (e.g. >4.0 mJ) result in rapid bubble 66 expansion that is more difficult to control and are accordingly, unsuitable for use with the present invention.

This description is given for purposes of illustration and explanation. It will be apparent to those skilled in the art that modifications and changes may be made to the invention described herein without departing from its scope or spirit.

I claim:
1. A midinfrared laser tissue ablater, comprising:
   a) a fiber optic cable having a first end and a second end;
   b) a radiation source optically connected to the first end of a fiber optic cable;
   c) a probe having a handle and a bifurcated cannula with a first half and a second half and a substantially closed, hollow tip having an opening opposite the handle;
   d) a fiber optic integrally and coaxially mounted in the probe, optically and mechanically connected to the second end of the fiber optic cable at the handle and terminating at a free end in an interior of the substantially closed, hollow tip, the free end having a coating with a hole so that a pulse of radiation emitted by the radiation source is directed through the fiber optic cable and the fiber optic to the free end where the pulse of radiation is reflected by the coating out the hole in the coating and into the opening of the tip;
   e) an irrigation source in fluid communication with the first half of the cannula; and
   f) an aspiration source in fluid communication with the second half of the cannula.
2. The laser tissue ablater of claim 1 wherein the radiation source is an Er:YAG laser.
3. The laser tissue ablater of claim 1 wherein the fiber optic cable comprises fluorozirconiate fiber.
4. The laser tissue ablater of claim 1 wherein the cannula comprises titanium.
5. The laser tissue ablater of claim 1 wherein the coating comprises gold.
6. The laser tissue ablater of claim 1 wherein the coating comprises silver.
7. The laser tissue ablater of claim 1 wherein the coating comprises enhanced aluminum.
8. The laser tissue ablater of claim 1 wherein the cannula fiber optic comprises low hydroxyl fused-silica.
9. The laser tissue ablater of claim 1 wherein the cannula fiber optic comprises low hydroxyl fused-silica.

* * * * *